US007951594B2

(12) United States Patent
Kong et al.

(10) Patent No.: US 7,951,594 B2
(45) Date of Patent: May 31, 2011

(54) METHOD OF CULTURING CONIFER SOMATIC EMBRYOS USING S(+)-ABSCISIC ACID

(75) Inventors: Lisheng Kong, Victoria (CA); Plamen Denchev, Victoria (CA); Reed Radley, Vancouver (CA); Irina I. Lobatcheva, Victoria (CA); Stephen M. Attree, Victoria (CA)

(73) Assignee: Cellfor Inc., Saanichton, British Columbia (CA)

( * ) Notice: Subject to any disclaimer, the term of this patent is extended or adjusted under 35 U.S.C. 154(b) by 656 days.

(21) Appl. No.: 11/528,560

(22) Filed: Sep. 28, 2006

(65) Prior Publication Data

US 2007/0101462 A1     May 3, 2007

Related U.S. Application Data

(60) Provisional application No. 60/723,921, filed on Oct. 6, 2005.

(51) Int. Cl.
    *C12N 5/00*          (2006.01)
    *C12N 5/02*          (2006.01)
    *A01H 11/00*        (2006.01)
    *A01H 9/00*         (2006.01)
    *A01H 5/00*         (2006.01)

(52) U.S. Cl. ..................... 435/422; 435/420; 435/430.1; 435/410; 800/295; 800/298

(58) Field of Classification Search .................. 435/422, 435/420, 430.1, 410; 800/295, 298
See application file for complete search history.

(56) References Cited

U.S. PATENT DOCUMENTS

| | | | |
|---|---|---|---|
| 5,034,326 A | 7/1991 | Pullman et al. | |
| 5,036,007 A | 7/1991 | Gupta et al. | |
| 5,187,092 A | 2/1993 | Uddin | |
| 5,236,841 A | 8/1993 | Gupta et al. | |
| 5,464,769 A * | 11/1995 | Attree et al. | 800/319 |
| 5,482,857 A | 1/1996 | Gupta et al. | |
| 5,506,136 A | 4/1996 | Becwar et al. | |
| 5,523,230 A | 6/1996 | Smith | |
| 5,565,355 A | 10/1996 | Smith | |
| 5,677,185 A | 10/1997 | Handley, III | |
| 5,856,191 A | 1/1999 | Handley, III | |
| 5,985,667 A | 11/1999 | Attree et al. | |
| 6,200,809 B1 | 3/2001 | Klimaszewska et al. | |
| 6,340,594 B1 | 1/2002 | Attree et al. | |
| 6,372,496 B1 | 4/2002 | Attree et al. | |
| 6,627,441 B1 * | 9/2003 | Attree | 435/422 |
| 2002/0192818 A1 | 12/2002 | Becwar et al. | |

FOREIGN PATENT DOCUMENTS

| | | |
|---|---|---|
| WO | WO 93/11660 A2 | 6/1993 |
| WO | WO 99/63805 A2 | 12/1999 |
| WO | WO 2004/065585 | 8/2004 |

OTHER PUBLICATIONS

Dunstan et al. Review Events Following ABA Treatment of Spruce Somatic Embryos. In Vitro Cell Dev. Biol. Plant 34 p. 159 1998.*
Ammirato (1983), "Embryogenesis", Handbook of Plant Cell Culture, vol. 1, pp. 82-123.
Hakman and Von Arnold (1988), "Somatic embryogenesis and plant regeneration from suspension cultures of *Picea glauca* (White spruce)", Physiologia Plantarum, 72:579-587.
Von Arnold and Hakman (1988), "Regulation of Somatic Embryo Development in *Picea abies* by Abscisic Acid (ABA)", J. Plant Physiol., 132:164-169.
Dunstan, et al. (1988), "Effects of Abscisic Acid and Analogues on the Maturation of White Spruce (*Picea glauca*) Somatic Embryos", Plant Science, 58:77-84.
Attree, et al. (1990), "Somatic embryo maturation, germination, and soil establishment of plants of black and white spruce (*Picea mariana* and *Picea glauca*)", Can. J. Bot., 68:2583-2589.
Roberts, et al. (1990), "Abscisic acid and indole-3-butyric acid regulation of maturation and accumulation of storage proteins in somatic embryos of interior spruce", Physiologia Plantarum, 78:355-360.
Dunstan, et al. (1991), "Racemic abscisic acid and abscisyl alcohol promote maturation of white spruce (*Picea glauca*) somatic embryos", Plant Science, 76:219-228.
Dong, et al. (1997), "Gene expression patterns, and uptake and fate of fed ABA in white spruce somatic embryo tissues during maturation", Journal of Experimental Botany, 48(307):277-287.
Dunstan, et al. (1997), "Abscisic acid [(+)-ABA] content in white spruce somatic embryo tissues related to concentration of fed ABA", J. Plant Physiol.
Kapik, et al. (1995), "Abscisic acid and zygotic embryogenesis in *Pinus taeda*", Tree Physiology, 15:485-490.
Kong, et al. (1997), "Changes of endogenous hormone levels in developing seeds, zygotic embryos and megagametophytes in *Picea glauca*", Physiologia Plantarum 101:23-30.
Pence, et al. (1981), "Sucrose-mediated regulation of fatty acid composition in asexual embryos of *Theobroma cacao*", Physiologia Plantarum, 53:378-384.
Avjioglu and Knox (1989), "Storage Lipid Accumulation by Zygotic and Somatic Embryos in Culture", Annals of Botany, 63:409-420.
Taylor, et al. (1990), "Storage-protein regulation and lipid accumulation in mocrospore embryos", Planta, 181:18-26.
Dutta and Appelqvist (1989), "The Effects of Different Cultural Conditions on the Accumulation of Depot Lipids Notably Petroselinic Acid During Somatic Embryogenesis in *Daucus carota* L.", Plant Science, 64:167-177.
Feirer, et al. (1989), "Triglycerides in embryogenic conifer calli: a comparison with zygotic embryos", Plant Cell Reports, 8:207-209.
Unyayar and Unyayar, "Production of Auxin and Abscisic Acid by *Phanerochaete chrysosporium* ME446 Immobilized on Polyurethane Foam", Turk J. Biol., 24(2000) 769-774.
Dunstan, et al. (1992), "Metabolism of (+)- and (−) abscisic acid by somatic embryo suspension cultures of white spruce", Phytochemistry 31(5):1451-1454.

(Continued)

*Primary Examiner* — Annette H Para

(57) ABSTRACT

A method for promoting maturation and development of vigorous conifer (gymnosperm) somatic embryos comprising the use of S(+)-ABA as the substantive form of ABA.

5 Claims, 3 Drawing Sheets

OTHER PUBLICATIONS

Jiang, et al. (1996), "Vicilin and Napin storage-protein gene promoters are responsive to abscisic acid in developing transgenic tobacco seed but lose sensitivity following premature desiccation", Plant Physiology, vol. 110, pp. 1135-1144.

Addicott et al., "Abscisic acid: a new name for abscisin II (dormin)," Science. Mar. 29, 1968; 159(822):1493.

Addicott et al., "Physiology of Abscisic Acid and Related Substances," Annu. Rev. Plant. Physiolol. 1969; 20:139-164.

Donnelly et al., Glossary of Plant Tissue Culture, Advances in Plant Sciences Series vol. 3, 1988, Dioscorides Press, Portland, Oregon, p. 9.

Hay et al., "Somatic Embryogenesis and Desiccation Tolerance in Conifers," "Somatic Embryogenesis in Woody Plants," pp. 72-73(1999), Jain MS, Gupta PK, Newton RJ eds., Kluwer Academic Publishers, AH Dordrecht, The Netherlands.

Norman et al., "Development of a Defined Medium for Growth of *Cercospora rosicola* Passerini," Appl. Environ. Microbiol., Jan. 1981; 41(1):334-336.

Özcan et al., "$GA_3$, ABA and Cytokinin Production by *Lentinus tigrinus* and *Laetiporus sulphureus* Fungi Cultured in the Medium of Olive Oil Mill Waste," Turk J Biol., 25 (2001) 453-462.

Addicott et al., "Abscisic acid," 1983, Praeger Publishers, pp. 81-82.

Singleton et al., Dictionary of Microbiology and Molecular Biology, $2^{nd}$ Ed., 1987, John Wiley and Sons, NY, p. 2.

Tautorus et al., "Somatic Embryogenesis in Conifers," Can. J. Bot., vol. 69, 1991.

Windsor et al., "The Uptake of (+)-S- and (−)-R-Abscisic Acid by Suspension Culture Cells of Hopbush (*Dodonaea viscose*)[1]," Plant Physiol. Sep. 1992; 100(1):54-62.

Dunstan, David I. et al., "Events following ABA treatment of spruce somatic embryos", In Vitro Cellular and Developmental Biology Plant, vol. 34, No. 2, Apr. 1998, pp. 159-168.

Attree, S.M. et al., "Embryogeny of gymnosperms: Advances in synthetic seed technology of conifers", Plant Cell Tissue and Organ Culture, vol. 35, No. 1, 1993, pp. 1-35.

Dong, Jin-Zhou et al., "Influences of altered phytohormone use on endogenous ABA and mRNA populations during white spruce (*Picea glauca*) somatic embryo culture", Tree Physiology, vol. 17, No. 1, 1997, pp. 53-57.

Stasolla, Claudio et al., "Maturation of somatic embryos in conifers: Morphogenesis, physiology, biochemistry, and molecular biology", In Vitro Cellular and Developmental Biology Plant, vol. 38, No. 2, Mar. 2002, pp. 93-105.

Supplementary European Search Report, EP1931766, Jul. 15, 2009.

Hill, R.D. et al., "Abscisic Acid Structure-Activity Relationships in Barley Aleurone Layers and Protoplasts", Plant Physiol. (1995) 108:573-579.

\* cited by examiner

METHOD OF CULTURING CONIFER SOMATIC EMBRYOS USING S(+)-ABSCISIC ACID

CROSS-REFERENCE TO RELATED APPLICATIONS

This application claims the priority right of our prior co-pending provisional application Ser. No. 60/723,921 filed Oct. 6, 2005.

BACKGROUND OF THE INVENTION

I. Field of the Invention

This invention relates to the culturing of somatic embryos, particularly those of gymnosperm plant species and especially conifers. More particularly, the invention relates to the culturing of somatic embryos in which abscisic acid (ABA) is employed for embryo development.

II. Description of the Prior Art

Somatic embryogenesis offers the potential to clonally produce large numbers of plants of many species at low cost. Somatic embryos develop without the surrounding nutritive tissues and protective seed coat found with zygotic embryos, so research has been directed to causing somatic embryos to functionally mimic seeds with regard to efficient storage and handling qualities. The development of techniques for somatic embryogenesis in conifers has greatly improved the ability to culture conifer tissues in vitro and now offers the means to clonally propagate commercially valuable conifers. However, it is necessary to further reduce production costs to make somatic embryogenesis affordable to industry. Thus, there is a need in the technology for improvement of the efficiency of embryo production and in the quality and vigor of plants resulting from somatic embryos from all species of conifers.

Somatic embryogenesis in plants is a multistage process consisting of induction, proliferation, maturation (embryo development), and germination, that requires specific culture conditions, including nutrient media compositions provided for each step of the multistep process. Thus, in general for most conifers, an auxin and cytokinin and a low osmoticum are required in media for induction and proliferation of embryogenic tissues. For further embryo development it is often beneficial to increase the osmotic concentration, and to replace the auxin and cytokinin with ABA.

Conifer somatic embryos appear different to somatic embryos of monocotyledonous and dicotyledonous species in that ABA should be supplied as early as possible in maturation protocols in order to promote embryo maturation. Merely reducing or eliminating auxin and cytokinin levels, as has been successful for maturation of somatic embryos of many angiosperm species (Ammirato 1983, Handbook of Plant Cell Culture, Vol. 1, pp. 82-123) led to infrequent or poor maturation in conifer embryos and more often resulted in browning and death of the immature somatic embryos. Furthermore, it appears that ABA should be applied for longer periods and at higher levels than generally applied to angiosperm somatic embryos.

There has been a trend for using increasingly higher concentrations of ABA to promote the maturation of conifer somatic embryos. This trend probably results from a need to inhibit precocious germination late in maturation which has become more apparent following the increasingly longer maturation times being used. Thus, ABA was first successfully used by Hakman and von Arnold 1988 (Physiol. Plant. 72:579-587) and von Arnold and Hakman 1988 (J. Plant Physiol. 132:164-169), at 7.6 µM. Dunstan et al. 1988 (Plant Sci. 58:77-84) subsequently found 12 µM ABA to be better. Shortly after, Attree et al. 1990 (Can. J. Bot. 68:2583-2589) reported that 16 µM was optimal. Roberts et al. 1990 (Physiologia Plantarum 78; 355-360) have shown that for some species of spruce, ABA at 30-40 µM could be used to promote maturation and yield mature embryos with storage protein polypeptides comparable to zygotic embryos. Such high levels were necessary to prevent precocious germination and allow maturation to proceed to later stages. Dunstan et al. 1991 (Plant Sci. 76:219-228) similarly found that high levels could permit embryo maturation. Unfortunately, high ABA levels used throughout the development period also increased the frequency of developmentally abnormal embryos. Subsequently, much higher ABA concentrations have been described. Becwar et al., U.S. Pat. No. 5,506,136 described ABA in development media at up to 120 µM. Dunstan et al., 1997 (Journal of Expt. Bot. 48, 277-287) suggested that a remedy to prevent precocious germination of conifer somatic embryos is to transfer cultures to fresh medium with ABA in the maturation culture period, as is commonly done. It is stated that exposure to fresh ABA is unlikely to lead to greatly improved yields of mature somatic embryos, unless the population of immature embryos remains sizable, but is more likely to lead to improvement in the quality of the mature somatic embryos through deposition of storage product and prevention of precocious germination. Dunstan et al. 1997 (J. Plant Physiol.) showed that the availability of ABA decreases during culture so can lead to precocious germination. They suggested that this is generally attributed to a low starting concentration of ABA, and the authors also suggest that extending the use of ABA during the maturation phase by periodic transfer to fresh nutrient medium will extend ABA availability. Uddin 1993 (U.S. Pat. No. 5,187,092) describes using various combinations and proportions of glucose, maltose, ABA and/or indolebutyric acid to promote maturation of conifer somatic embryos. This patent suggests that conifer somatic embryos should be cultured in the presence of at least 3% maltose and at least 10 µM ABA.

Attree et al (U.S. Pat. No. 5,464,769) described the combined use of a water stress and ABA during the embryo maturation process to stimulate maturation frequencies and promote further maturation of the embryos, and to increase dry weight and lower moisture content, leading to desiccation tolerance. Constant levels of ABA were maintained during development of the embryos. With regard to the non-plasmolysing water stress, a non-plasmolysing high molecular weight compound such as PEG, however, other non-plasmolysing water stresses such as environmental stresses or increased gelling agent were also suggested, and increased gelling agent was also described in U.S. Pat. No. 6,200,809.

Kapik et al. 1995 (Tree Physiology 15, 485-490), and Kong et al., 1997 (Physiologia Plantarum 101, 23-30) showed that endogenous ABA rises during seed and zygotic embryo development then falls during late development. Therefore, it was suggested that ABA should be moderately high at the start of development then decreased throughout development to low levels or to zero at the end of the culture period, so promoting germination.

Thus, in U.S. Pat. No. 5,034,326 Pullman et al. (1991) describe a method for developing tissue culture induced coniferous somatic embryos into well-developed cotyledonary embryos. The method comprises a multi-stage culturing process in which early stage embryos are cultured on a late stage medium comprising a significantly higher osmotic potential along with moderately high ABA and an absorbent material to gradually reduce the level of available ABA over time. A critical aspect of this method lies in the inclusion of the absorbent material in the embryo development medium. Absorbent materials suggested include activated charcoal and silicates. The absorbent is used to slowly reduce the ABA and remove metabolic waste products. The purpose of this reduction in ABA was to follow the natural tendency in embryo development. It was suggested that as development approaches completion, the presence of lesser amounts of ABA is required. Similarly Gupta et al. (1991) in U.S. Pat. No. 5,036,007 describe a similar method. In Douglas fir culture ABA is reduced from about 10-20 µM at the start of development to less than about 3 µM or even to zero.

A similar method was described in U.S. Pat. No. 5,236,841, by Gupta et al. (1993), however, the invention relates to the use of gradually decreasing amounts of the plant hormone abscisic acid during the time when the embryos are further developed into cotyledonary embryos by stepwise subcultures. It was suggested that when transfers to fresh medium are made that the initial ABA level of the fresh medium should not be higher than the final level of the medium at the end of the preceding culture period. More recently, however, Gupta et al. (1996) in U.S. Pat. No. 5,482,857 found that when using activated charcoal ABA was not necessary for cotyledonary embryo development of Douglas fir.

U.S. Pat. No. 6,627,441 describes a method for producing viable mature conifer somatic embryos consisting of water stressing the somatic embryos in medium containing ABA that is increasing during development including towards the mid point of cotyledonary development when the tendency for precocious germination is the highest prior to water contents becoming sufficiently low. Also envisaged is a method where the ABA is rising progressively throughout development.

It has been suggested to use abscisic acid (ABA) or osmoticum for enhancing storage levels in plant cells. For example, it was shown that somatic embryos of *Theobroma cacao* could be induced to accumulate fatty acids approaching the composition of commercial cocoa butter by using a high sucrose concentration in the culture medium (Pence et al. 1981; Physiol. Plant. 53:378-384). Modifying the culture conditions by osmoticum concentration and/or ABA content similarly improved lipid accumulation in *Brassica napus* L. somatic (Avjioglu and Knox 1989; Ann. Bot. 63:409-420) and microspore (Taylor et al. 1990; Planta 181: 18-26) derived embryos as well as somatic embryos of carrot (Dutta and Appelqvist 1989; Plant Sci. 64: 167-177) and celery. Also, the level of storage lipids in *P. abies* somatic embryos was improved by optimising the ABA level to between 10-20 µm, but the somatic embryos contained about 4% of the lipid level obtained by zygotic embryos (Feirer et al. 1989; Plant Cell Rep. 8:207-209).

Embryo drying occurs naturally in most seeds, and has a role to play in the developmental transition between maturation and germination. Thus, desiccation led to enhanced germination of both zygotic and somatic embryos. Desiccation of whole somatic embryos is also an alternative method of germplasm storage. Somatic embryos produced continuously year-round could therefore be dried and stored until the appropriate planting season, or shipped to new locations. Conifer embryos treated with ABA and water stress can survive desiccation to low moisture contents (U.S. Pat. Nos. 5,464,769, 5,985,667, 6,340,594, 6,372,496).

ABA has also been used to in induction and maintenance media to promote induction and proliferation of conifer somatic embryos (U.S. Pat. Nos. 5,677,185, 5,856,191 and U.S. patent application 2002/0192818).

All of the above examples involving embryo tissue culture used synthetically produced and commercially available racemic ABA which consisted of 50% mixtures of (+)-ABA (S-ABA) and (−)-ABA (R-ABA). (−)-ABA is not biologically inert—it has hormonal activity in many bioassays, and is degraded by a different route in plant tissues from (+)-ABA—and at a substantially different rate (usually much slower). The effect of pure S(+)-ABA on conifer somatic embryogenesis is largely unknown. Dunstan et al. 1992 did compare a pure sample of S(+)-ABA with racemic on somatic embryos of spruce liquid suspension cultures and showed that the S(+)-ABA was metabolized completely into phaseic acid within seven days. The R(−)-ABA remained unchanged. The cultures were only treated for a maximum of eight days and no mature embryos were recovered and seedlings grown and no benefit was suggested for using S(+)-ABA over the racemic S,R(±)-ABA form.

The development of techniques for somatic embryogenesis in conifers has greatly improved the ability to culture conifer tissues in vitro and now offers the means to clonally propagate commercially valuable conifers. However, it is necessary to further reduce production costs to make somatic embryogenesis affordable to industry. Thus, there is a need in the technology for improvement of the efficiency of embryo production and of the quality and vigour of plants resulting from somatic embryos from all species of conifers.

SUMMARY OF THE INVENTION

In general, the invention provides a method for promoting maturation and development of vigorous conifer (gymnosperm) somatic embryos comprising the use of S(+)-ABA as the substantive form of ABA.

According to one exemplary embodiment, there is provided a method of subjecting a gymnosperm somatic embryo to a step of somatic embryogenesis, which method involves contacting the embryo with a culture medium (liquid, semi-solid or solid) containing an effective amount of abscisic acid (ABA) for said step, wherein said ABA present in the liquid medium comprises an excess of S(+)-abscisic acid (S-ABA) relative to any other isomer of ABA. Preferably, the S-ABA is (in increasing order of desirability) at least 55%, 60%, 65%, 70%, 75%, 80%, 85%, 90%, 95%, 99% or 100% by weight of total ABA, and desirably, at least 75% by weight.

Most preferably, the ABA present in the medium comprises only S-ABA, and the S-ABA is a synthetic or natural analogue, e.g. an analogue derived from a microorganism, such as a fungus.

The gymnosperm somatic embryo with which the invention may be used is preferably a conifer, e.g. *Pinus taeda* (loblolly pine), *Pinus radiata* (radiata pine) and *Pseudotsuga menziesii* (Douglas fir), and the method is preferably applied to a maturation step, including pre-maturation.

Because the S-ABA is found to be more effective when used alone than in a racemic mixture, at least for some steps of somatic embryogenesis, the ABA may be used in an amount of less than 50% of the minimum amount of conventional S,R-ABA required for the same step.

Other exemplary embodiments of the invention include a method of promoting maturation and development of vigorous conifer (gymnosperm) somatic embryos of less than 55% moisture content comprising the use of S(+)-ABA as the substantive form of ABA; a method of promoting maturation and development of vigorous conifer (gymnosperm) somatic embryos comprising the use of S(+)-ABA as the substantive form of ABA together with a water stress to promote the development of embryos to less than 55% moisture content; a method of promoting maturation and development of vigorous conifer (gymnosperm) somatic embryos comprising the use of S(+)-ABA, wherein the S(+)-ABA comprises greater than 50% of the total ABA forms provided to the embryos; and a method of culturing embryogenic tissue in which any of the culture steps comprises the use of S(+)-ABA as the substantive form of ABA.

The embryos are optionally subsequently desiccated to less than 30% moisture content.

DEFINITIONS

Figure 1:
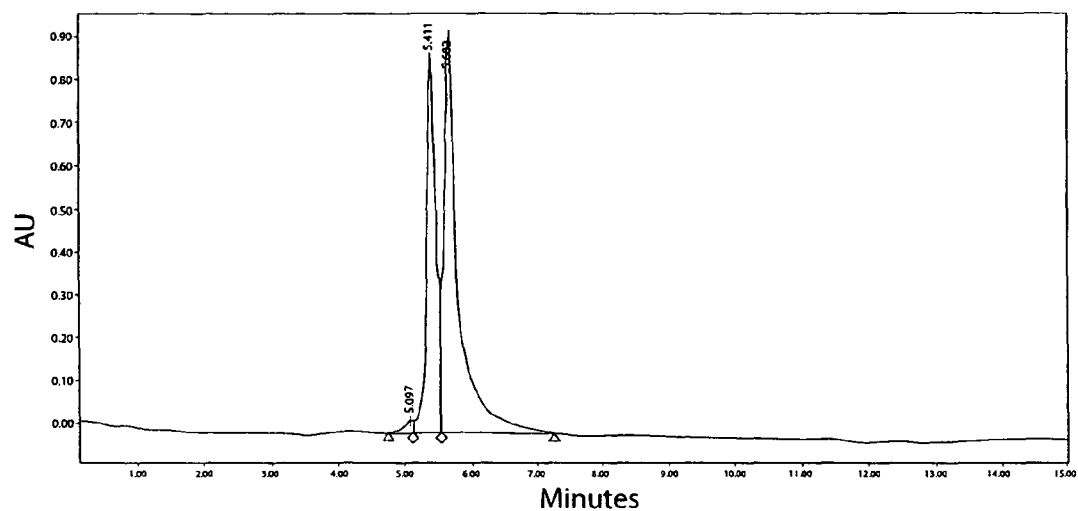
FIG. 1 is a chromatograph showing racemic S,R-ABA with the two major peaks at retention times of 5.41 and 5.68 representing S(+)-ABA (left) and R(−)-ABA (right)

The following definitions are consistent with the usage of terms in the present specification.

Abscisic Acid (ABA): A plant growth regulator in the group of stress hormones.

S,R-ABA: Traditionally commercial ABA. This is a racemic mixture of the (+) and (−) forms ((±)-ABA).

S-ABA: The naturally occurring form of ABA designated (+)-cis,trans-Abscisic Acid; Also known as (S)(+)-Abscisic Acid or (S)(+)-ABA; Molecular formula: $C_{15}H_{20}O_4$; Formula weight: 264.3. The chemical structure of the natural hormone S(+)-Abscisic Acid is shown below:

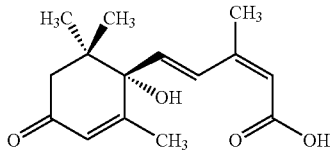

Auxin: A plant growth regulator which may be natural or synthetic. The main physiological effect of auxin is to stimulate cell elongation. Examples are indole acetic acid (IAA) and 2,4-dichlorophenoxyacetic acid (2,4-D).

Clone: When used in the context of plant propagation, the term refers to a collection of individuals having the same genetic constitution (genotype), and is produced from a culture that arises from an individual explant.

Conversion: The ability of a somatic embryo to germinate (either in vitro or ex vitro) and subsequently develop into an established, autotrophic plant with root and needles.

Cytokinin: A natural or synthetic plant growth regulator such as benzyl adenine (BA). The main physiological effect of cytokinin is to stimulate meristematic cell division.

Desiccation: The drying of an embryo by any means to a moisture content less than that of the original hydrated embryo. Desiccation processes may include (a) mild desiccation, which encompasses moisture contents in the 36-55% moisture content range, and (b) severe desiccation, which occurs at moisture contents less than 36%, usually in the range of 5-30%. A fully desiccated viable embryo is able to survive freezing, and after rehydration, is able to successfully complete the germination process and convert to a normal autotrophic plant.

Embryogenic culture: A plant cell or tissue culture capable of forming somatic embryos and regenerating plants via somatic embryogenesis.

Explant: Organs, tissues or cells derived from a plant and cultured in vitro for the purposes of starting a plant cell or tissue culture.

Galactose: A hexose of the formula $CH_2OH.(CHOH)_4 CHO$. It is present in certain gums and seaweeds as a polysaccharide galactan and as a normal constituent of milk.

Lactose: Lactose is a disaccharide ($C_{12}H_{22}O_{11}$). It yields D-glucose and D-galactose on hydrolysis, which is catalysed by lactase.

Line: This is another term for "clone".

Mature embryo: A mature embryo is one which is capable of germination, given the necessary environmental conditions (temperature, light, water, nutrients, etc.). The term implies that the embryo has undergone development through various developmental stages and has reached a size and stage suitable for germination. The embryo contains storage proteins, lipids, and if provided with suitable maturation conditions (e.g. ABA and water stress), will be desiccation tolerant, so may be desiccated prior to germination.

Megagametophyte: A haploid nutritive tissue of gymnosperm seed, of maternal origin, within which the gymnosperm zygotic embryos develop.

Moisture content: The amount of water present in an embryo. This is generally measured by weighing an embryo before and after oven drying (FW and DW, respectively). The preferred manner of expression is percentage weight of water based on the original weight of the embryo, so that the values are always less than 100. MC=((FW−DW)/FW)×100%

Prematuration: The step following the proliferation step and prior to the maturation step, usually involving a gradual reduction in the concentrations of one or more of the hormones auxin and cytokinin and/or a change in water stress and the addition of ABA.

Proliferation: The steps following induction prior to maturation, in which embryogenic cultures divide and grow but do not develop into mature embryo stages. The proliferation step may also be referred to as the maintenance step.

Nutrients: The inorganic micro- and macro-minerals, vitamins, hormones, organic supplements, and carbohydrates (or any one or more of them) necessary for culture growth and somatic embryo germination.

Somatic embryo: A plant embryo formed in vitro from vegetative (somatic) cells by mitotic division of cells. Early stage somatic embryos are morphologically similar to immature zygotic embryos, and comprise a region of embryonal cells subtended by suspensor cells.

Somatic Embryogenesis: A process of initiation and development of somatic embryos in vitro from somatic cells and tissues.

Water potential: The total water potential to which an organism is subjected in a water-containing matrix. This is a sum of (1) osmotic (solute) potential, (2) gravitational potential resulting from the vertical position of the water, and (3) a suction component (capillary or matric potential).

Water Stressing: The reduction of water potential to which an embryogenic tissue or somatic embryo is controlled during maturation by controlling the environment of the tissue or embryo in order to modify the progress of maturation.

Zygotic Embryo: An embryo derived from the sexual fusion of gametic cells produced by meiosis.

DESCRIPTION OF THE PREFERRED EMBODIMENTS

Somatic embryogenesis in plants is a multi-step process consisting of induction, proliferation, maturation (embryo development), and germination, and it requires that specific culture conditions, including nutrient media compositions, are provided for each step of the multi-step process. Thus, in general for most conifers, an auxin and cytokinin and a low osmoticum are required in media for induction and proliferation of embryogenic tissues. For further embryo development, it is often beneficial to increase the osmotic concentration, and to replace the auxin and cytokinin with ABA.

Diploid cultures of conifers are most readily initiated from zygotic embryos, which are genetically dissimilar from each other. Low osmotic conditions are beneficial for induction from conifers. The sugar most often used for induction is sucrose at about 1% (w/v) concentration. However, the use of galactose-containing compounds, such as galactose and lactose at the induction stage, was shown to lead to improved induction success (PCT patent application WO 2004/065585). The most suitable concentration may be less than about 6%, and, more particularly, may be less than about 2%, and even more particularly, between about 1% and about 2%, alone or with additional carbon sources. Cytokinin is important to most species, and is usually included with an auxin at concentrations of 5 and 10 µM, respectively.

Genotype specificity for embryogenic induction occurs in conifers. Also, the induction of somatic embryogenesis is under strong additive genetic control. For conifers, immature zygotic embryos yield somatic embryos more readily than mature zygotic embryos, which are generally more responsive than explants from young seedlings. Cryopreservation of immature somatic embryos in liquid nitrogen is routine for long-term preservation and is used to preserve genotypes while extended field tests are carried out. Following the field trials, elite genotypes are then removed from cryogenic storage and bulked up in liquid suspensions for mass propagation.

Embryogenic cultures of conifers are usually maintained on a medium similar to the induction medium, which typically includes an auxin, a cytokinin and a low concentration of sugar. The method of maintenance (or proliferation) depends upon the intended use of the culture. A common way to maintain cultures is on semi-solidified medium in Petri dishes. These stationary cultures are sub-cultured every 2-4 weeks to prevent browning and death. Liquid culture is more suitable for maintaining conifer cultures in a rapidly proliferating state for large scale propagation.

Pine embryogenic tissue, when grown on ABA in the presence of sucrose, undergoes a disorganized growth phase, prior to organized growth. Such cultures do not readily undergo further development with ABA and a low osmotic concentration, perhaps because they are too juvenile to respond to ABA. Including lactose or galactose at the proliferation step has the benefit of reducing disorganized growth, and leads to the production of well-organized immature embryos with enlarged embryonal regions (PCT patent application WO 2004/065585). The inclusion of 1% sucrose with the lactose or galactose helps to improve proliferation rates. This effect of lactose or galactose on improving embryo organization is more pronounced than with maltose. When transferred to maturation medium these lactose/galactose embryos have a greater propensity to develop to mature embryo stages than those grown on other sugars, including maltose, and disorganized suspensor tissue proliferation is inhibited. The result is that mature embryos are produced in higher yields than with other known methods, and the mature embryos are of greater uniformity. They are also of better quality and thus are vigorous during subsequent germination. All of the latter lead to greater numbers of plants recovered at the end of the process.

In order to encourage the production of mature developmental stages of conifer somatic embryos, immature somatic embryos must be transferred from a medium containing hormones to stimulate proliferation to an environment containing ABA and ideally a raised osmotic concentration. A gradual transition to these growth conditions is often beneficial. Thus, prior to ABA treatments, immature somatic embryos may be transferred to a pre-maturation medium containing no, or reduced, plant growth regulators. Charcoal may be beneficial. The ABA used for culturing conifers until now has been S,R-ABA, i.e. commercially produced mixtures of (±) racemic ABA, in which the (±)-ABA and (−)-ABA enantiomers are present in approximately equal proportions.

The newly-discovered fact that embryos of at least some conifer species can show improved maturation frequencies and germination vigor following maturation in S(+)-ABA alone is an unexpected beneficial result. The method is especially well suited to culturing conifers of the family Pinaceae, especially those species including *Pinus taeda* (loblolly pine), *Pinus radiata* (radiata pine) and *Pseudotsuga menziesii* (Douglas fir). The method produces higher maturation and germination frequencies. This results in lower costs and also results in a higher number of genotypes that can be mass produced. It is expected that S-ABA used in induction and maintenance media also leads to greater response in induction and proliferation rates.

S-ABA is commercially available and is produced by certain fungi, e.g. *Phanerochaete chrysosporium*, a resupinate fungus that decays wood by degrading lignin. Ünyayar and Ünyayar of Mersin Univesity, Mersin-Turkey have described a method of producing ABA utilizing immobilized cell culture ("Production of Auxin and Abscisic Acid by *Phanerochaete chrysosporium* ME446 Immobilized on Polyurethane Foam", Turk J. Biol, 24(2000) 769-774, the disclosure of which is incorporated herein by reference). Basically, mycelia were attached to cubes of polyethylene foam submerged in growth medium (stock basal mineral, SBM) and growth was allowed to proceed throughout the foam. ABA and auxins were then extracted from the culture medium. Of course, S-ABA can also be produced by separation of isomers from the racemic mixture, e.g. by high pressure liquid chromatography, although this is not preferred due to the high cost and low quantities obtained.

Given the improved results obtained by using S-ABA alone, there is no reason to use S-ABA in combination with S,R-ABA. However, the use of S-ABA in combination with some S,R-ABA is not precluded in this invention. If such a combination is used, there will always be an excess of S-ABA because S,R-ABA comprises an approximately 50:50 mixture of the (+) and (−) forms of ABA.

Following the maturation step it is often desirable to desiccate the somatic embryos. A moisture content of less than 55% is beneficial to producing high storage reserves and inducing desiccation tolerance. In addition to promoting germination, desiccation reduces production costs by providing a means of storing somatic embryos. For optimal efficiency, mature somatic embryos can be produced continuously year round, then stored and pooled with somatic embryos from subsequent production runs. They can then be germinated synchronously to provide plants of uniform age and size for planting during a suitable growing season.

Post-germinative growth of conifer somatic embryos occurs without the benefit of the haploid megagametophyte, which is a major organ for storage of both lipids and proteins within the conifer seed. Conifer somatic embryos therefore require nutrients, usually in the form of PGR-free media supplied at half strength and containing 2-3% sucrose for further growth into autotrophic plants.

The process of the present invention is not limited to any single basal culture medium. Any well known medium or modification may be used; however, we have found the formulation in Table 1 to work well for many conifers as described in the following sections.

TABLE 1

TX medium basal salts

| Basal salts | Amount per liter Medium, mg |
|---|---|
| Major | |
| $KNO_3$ | 950.00 |
| $KH_2PO_4$ | 170.00 |
| $MgSO_4 \cdot 7H_2O$ | 925.00 |
| $CaCl_2 \cdot 2H_2O$ | 211.00 |
| Minor | |
| KI | 4.15 |
| $H_3BO_3$ | 31.0000 |
| $ZnSO_4 \cdot 7H_2O$ | 43.0000 |
| $MnSO_4 \cdot H_2O$ | 21.0000 |
| $Na_2MoO_4 \cdot 2H_2O$ | 1.5000 |
| $CuSO_4 \cdot 5H_2O$ | 0.5000 |
| $CoCl_2 \cdot 6H_2O$ | 0.1300 |
| Iron | |
| $FeSO_4 \cdot 7H_2O$ | 27.8 |
| $Na_2EDTA$ | 37.2 |
| Vitamins | |
| Thiamine-HCl | 0.1000 |
| Pyridoxine-HCl | 0.1000 |
| Nicotinic acid | 0.5000 |
| Myo-Inositol | 100 |

EXAMPLE 1

Analysis of Ratio of (+)-ABA and (−)-ABA in ABA Samples by HPLC

Figure 2:
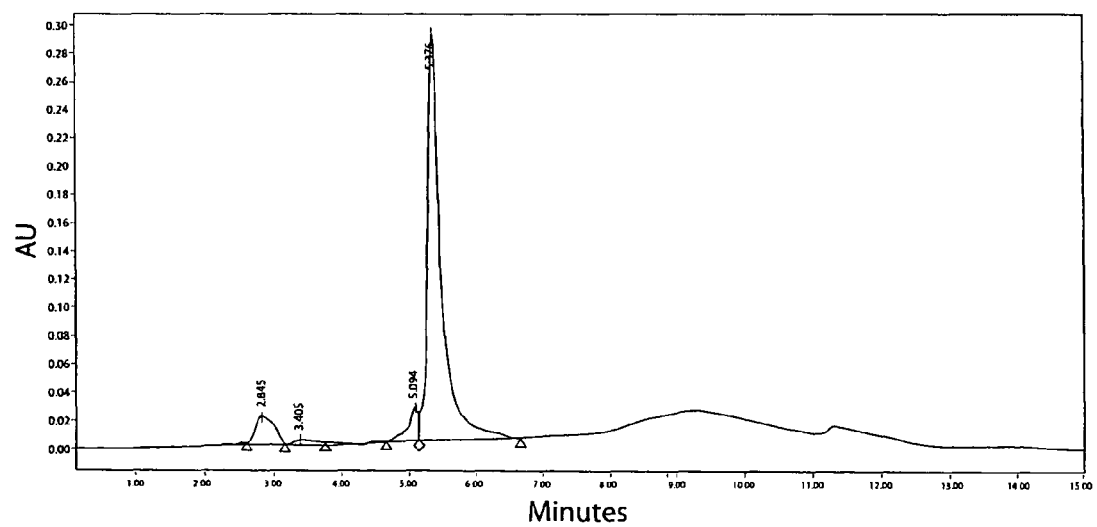
FIG. 2 is a chromatograph showing S(+)-ABA with only one major peak at a retention time of 5.376.

Sample Preparation
15 For each sample, ABA powder of 0.0264 g was dissolved in 9.1 mL MeOH to make a final concentration of 10 mM ABA sample. The 10 mM samples were used directly for total ABA analysis, but had to be diluted further to a 1 mM concentration for separation into (+) and (−) ABA.
ABA Liquid Stock (Controls and Standards)
   10 mM 98% racemic ABA stock
   10 mM 90% S-ABA stock
   1 mM 98% racemic ABA standard prepared by dissolving 0.0264 g powder in 100 mL MeOH
   1 mM 90% S-ABA stock prepared by diluting 10 mM 90% stock into 10 mL MeOH
HPLC Analysis
   Samples of 5 µl volume were injected into the HPLC system with the Symmetry $C_{18}$ column for total ABA and 2 µl samples were injected into (R,R)Whelk-O,1 column to separate (+) and (−) ABA. ABA was detected by PDA at 254 nm wavelength.
Results
   FIG. 1 shows is a chromatograph showing that the racemic ABA is composed of 2 peaks of equal proportions of (+) and (−)ABA. The two major peaks at retention time of 5.41 and 5.68 represent S-ABA (left) and R-ABA (right).
   FIG. 2 is a chromatograph showing S(+)-ABA with only one major peak at retention time of 5.376.

EXAMPLE 2

Comparison of Pure S-ABA and S,R-ABA on Douglas Fir Somatic Embryogenesis

The culture medium used for Douglas fir was TX medium (see Table 1) with the following additives: glutamine 100 mg/L, casein hydrolysate 100 mg/L, and pH 5.8. The following compounds were added into the basal medium for Douglas fir somatic embryo development at different stages:
   1) Solid maintenance medium: 9 µM 2,4-D and 4.5 µM BA, gellan gum 0.28%, sucrose 1%.
   2) Liquid maintenance and bulking-up medium: 9 µM 2,4-D and 4.5 µM BA, different carbon sources for experiments.
   3) Liquid pre-treatment medium: 20 (first week) or 30 µM ABA (second week), 10% PEG4000 (first week) or PEG1500 (second week), different carbon sources as described in examples below.
   4) Solid maturation medium consisted of three media all with 0.02% $NH_4NO_3$ and the following:
      Medium I. 40 µM ABA, 10% PEG 1500, maltose 2.5%, gellan gum 0.6%
      Medium II. 60 µM ABA, 10% PEG1500, maltose 2.5% and sucrose 1%, gellan gum 0.8%
      Medium III. 70 µM ABA, 6% PEG1500, sucrose 6%, gellan gum 1%.

Figure 3:
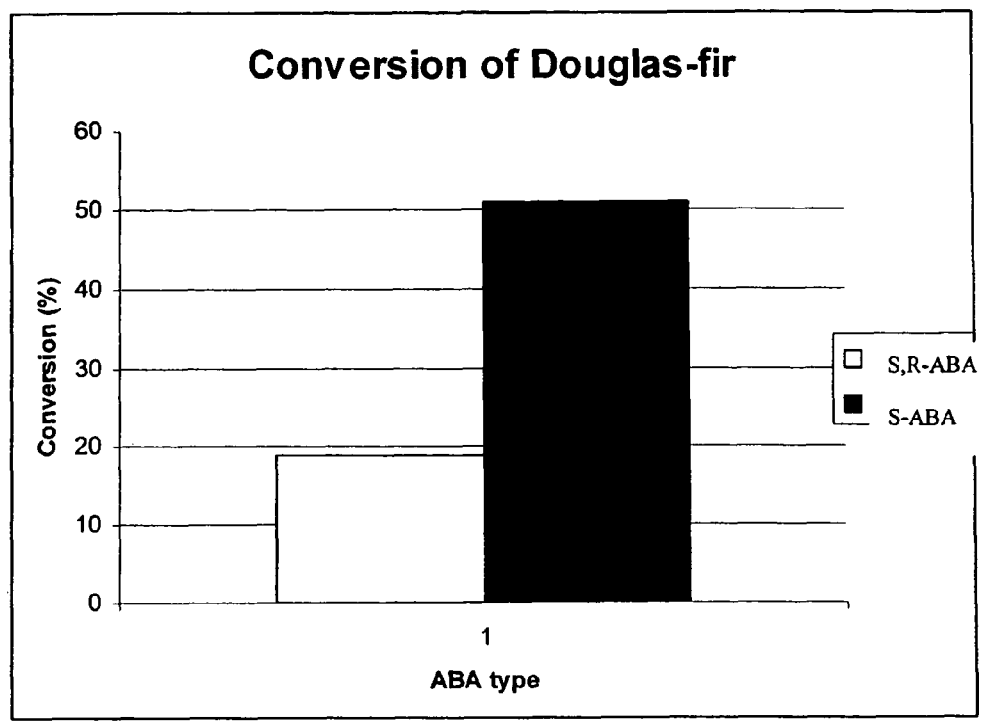
FIG. 3 is a graph showing one cell line which showed low conversion potential in which conversion of embryos cultured on S-ABA increased 2.5 fold compared to S,R-ABA.

The culture was kept in darkness at 23° C. Embryogenic tissue was sub-cultured once every two weeks onto solid maintenance medium. Plant tissue was then bulked up in liquid culture using protocols described previously (galactose patent). The solid and liquid multiplication media contained (1% sucrose, galactose) as the carbon source. Solid maturation for Douglas-fir followed a regular protocol that included (after plating out at 0.3 grams per large petri-plate) three transfers on different media types at 2 weeks, 5 weeks and 8 weeks. All petri-plates were transferred to 12° C. after the third transfer where they would remain for 1 week followed by desiccation for 3 weeks. Following desiccation, the plates were stored for 1 week.
   5) Germination. The cultures were germinated at room temperature for 2 to 3 weeks on TX medium (Table 1), 0.5% gellan gum, 1 g/L $NH_4NO_3$ after which the germinants were hand selected and placed in low-light for 1 week and high-light for 7 weeks then planted in miniplugs and evaluated after 14 weeks.
Douglas Fir Results
   The results showed that the effect on maturation frequencies was similar for the ABA types; however, the S-ABA had a pronounced effect on conversion. FIG. 3 shows one cell line which showed low conversion potential in which conversion of embryos cultured on S-ABA increased 2.5 fold compared to S,R-ABA.

EXAMPLE 3

The culture medium for loblolly pine was TX medium (see Table 1) with the following additives: Glutamine 2500 mg/L, casein hydrolysate 3000 mg/L, and pH 5.8. The following compounds were added into the basal medium for loblolly pine somatic embryo development at different stages:

1) Solid maintenance medium: 9 μM 2,4-D and 4.5 μM BA, gellan gum 0.3%, sucrose 1%, lactose 2%.

2) Liquid maintenance and bulking-up medium: 9 μM 2,4-D and 4.5 μM BA, 1% sucrose, 2% lactose.

3) Liquid pre-treatment medium: 1% sucrose, 2% lactose.

4) Preculture II medium. Lactose 2%, 1% sucrose

5) Solid maturation containing 1% gellan gum, and 2500 mg/L L-glutamine and 3000 mg/L casein hydrolysate, 3% sucrose. The maturation media contained different types of ABA and concentrations. S,R-ABA (98% purity) was tested at the previously determined optimum of 120 μM. S-ABA (90% purity) was tested at 60 μM and 120 μM. 0.3 grams of tissue were plated per petri-plate). Culture was for 18 weeks in the dark at room temperature. After, the embryos were desiccated for 1.5 hours in a stream of sterile air to a moisture content of less than 10%. Plates were stored at −28° C.

6) Germination. The filter papers with desiccated embryos attached were moved onto germination medium shown in Table 2, and cultured in the dark for 1 week then transferred to light. The numbers of germinants of suitable quality for planting were counted.

TABLE 2

Medium used for germination of loblolly pine.

| Activated charcoal | 1000 |
| Agar | 6000 |
| Ca(NO3)2•4H2O | 354 |
| CuSO4•5H2O | 8 |
| H3BO3 | 6 |
| KH2PO4 | 212 |
| KNO3 | 258 |
| L-Glutamine | 200 |
| MgSO4•7H2O | 506 |
| MnSO4•H2O | 0.3 |
| myo-Inositol | 100 |
| Na2MoO4•2H2O | 0.02 |
| Nicotinic acid | 0.5 |
| Plant Product iron | 80 |
| Pyridoxine-HCl | 0.1 |
| Sucrose | 20000 |
| Thiamine-HCl | 0.1 |

Loblolly Pine Results

Figure 4:
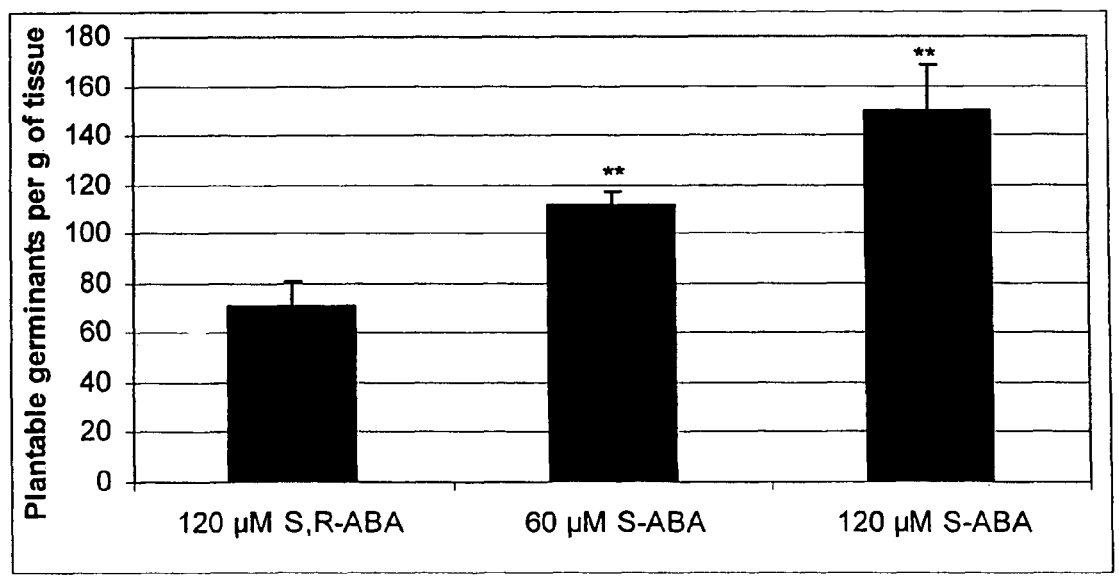
FIG. 4 is a graph showing S-ABA vs. S,R-ABA plantable germinants per gram of tissue plated for loblolly line 76.

FIG. 4 shows the effect of the different types of ABA and concentration.

The figure compares S-ABA vs. S,R-ABA plantable germinants per gram of tissue plated for loblolly line 76.

60 μM S-ABA yielded significantly higher number of plantable germinants per gram of tissue plated than the 120 μm S,R-ABA; however, the 120 μM S-ABA led to double the number of plantable germinants compared to the 120 μM S,R-ABA. The 60 μM S-ABA treatment contains the same concentration of S-ABA as the S,R-ABA treatment, suggesting that the (−)-ABA present in the S,R-ABA has an inhibitory effect on the frequency of embryos that develop, and their transition into germinants. It would have been expected that the purer S-ABA would have an optimum concentration about half of the S,R-ABA optimum. The 60 μM S-ABA treatment was not equal to the S,R-ABA treatment, but was in fact better, and the 120 μM S-ABA treatment was even more optimal. This is a novel and very unexpected result.

EXAMPLE 4

The effect of the different kinds of ABA on the survival and vigour of germinants was investigated. The germinants were prepared as described above except that ABA in the maturation medium consisted of 95% and 98% purity S-ABA, which was used in the maturation medium at 60 and 120 μM concentration. The S,R-ABA (98% purity) was used at 60 and 120 μM concentration. Miniplug seedlings of merchantable quality were scored after 14 weeks in the nursery.

Figure 5:
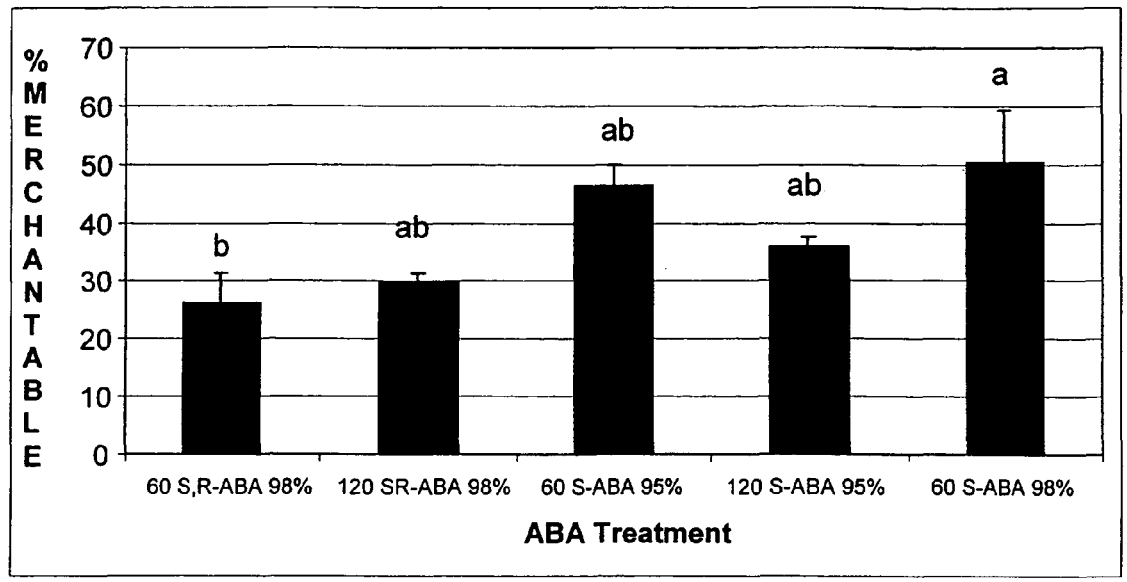
FIG. 5 is a graph showing Line 76 merchantable seedlings in nursery following maturation treatments with S- or S,R-ABA of different concentrations and purity.

The results are shown in FIG. 5. This shows Line 76 merchantable seedlings in the nursery following maturation treatments with S- or S,R-ABA of different concentrations and purity.

120 μM S-ABA treatment was more optimal than the 60 μM S,R-ABA treatment. The S-ABA treatments all yielded higher mean % merchantable than the S,R-ABA treatments with the 60 μM 98% purity S-ABA being significantly the highest.

EXAMPLE 5

The effect of S-ABA (95% purity) was tested in the loblolly pine pre-culture II medium followed by maturation medium. Somatic embryos of line 76 were cultured as described above; however, ABA was added to the pre-culture medium and maturation medium in the following treatments:

TABLE 3

| Preculture medium | Maturation medium |
| --- | --- |
| 45 μM S-ABA | 90 μM S-ABA |
| 90 μM S-ABA | 90 μM S-ABA |
| 90 μM S-ABA | 120 μM S-ABA |
| 90 μM S-ABA | 120 μM R-ABA |

Figure 6:
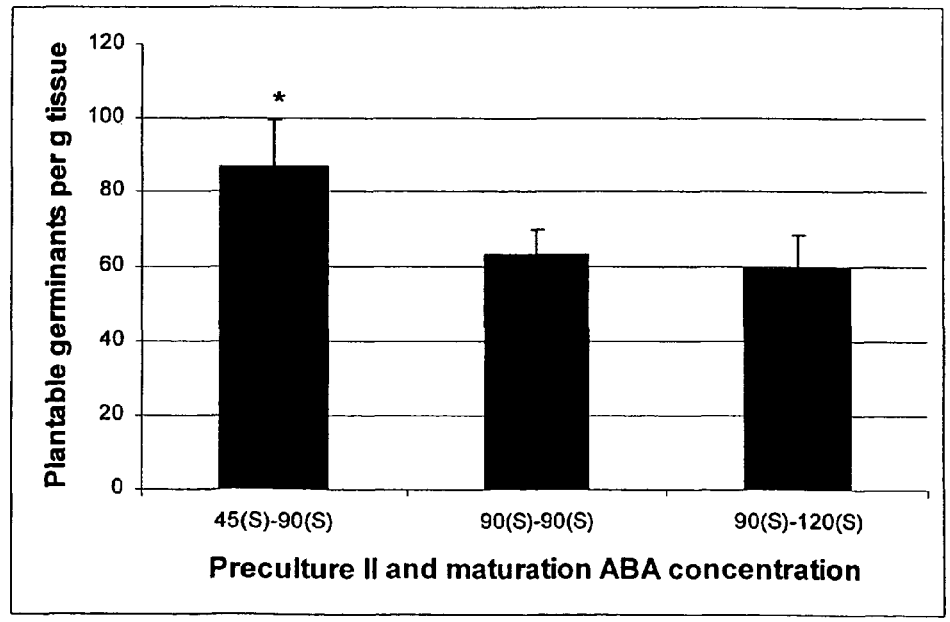
FIG. 6 is a graph showing the effect of S-ABA concentration in preculture II medium and maturation medium.

The results are shown in FIG. 6, which shows the effect of S-ABA concentration in preculture II medium and maturation medium.

Results show that a gradual increase in S-ABA from 45 μM in the pre-culture medium to 90 μM in the maturation medium was superior to constant ABA throughout development. Increasing ABA was described in U.S. Pat. No. 6,627,441. The 90 μM S-ABA maturation medium was superior to the 120 μM S-ABA maturation medium.

What we claim is:

1. A method of promoting maturation of vigorous conifer somatic embryos, wherein the method comprises subjecting immature conifer somatic embryos of loblolly pine or Douglas fir to culture conditions effective for maturation of the embryos, including exposing the embryos to a culture medium containing ABA, wherein S(+)-ABA is used alone in the culture medium as said ABA or is used in excess of any other isomer of said ABA present in the culture medium, and subjecting the embryos to water stress to promote the development of viable embryos having a moisture content in a range of 3.1% to less than 55%.

2. The method of claim 1, in which the embryos are desiccated to a moisture content in a range of 3.1% to less than 30%.

3. The method of claim 1, in which S-ABA is present at greater than 90% of the total ABA.

4. The method of claim 1, in which the S-ABA is present at greater than 76% of total ABA.

5. The method of claim 1, wherein the embryos are subjected to water stress to promote the development of embryos to a moisture content in a range of 5 to less than 55%.

* * * * *